United States Patent
Sun et al.

(10) Patent No.: US 6,952,611 B2
(45) Date of Patent: Oct. 4, 2005

(54) METHOD FOR ASSESSING CARDIAC FUNCTIONAL STATUS

(75) Inventors: Weimin Sun, Plymouth, MN (US); Veerichetty Kadhiresan, Lino Lakes, MN (US); Bruce H. KenKnight, Maple Grove, MN (US); Richard S. Sanders, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 528 days.

(21) Appl. No.: 10/136,910

(22) Filed: Apr. 30, 2002

(65) Prior Publication Data

US 2002/0123772 A1 Sep. 5, 2002

Related U.S. Application Data

(62) Division of application No. 09/551,310, filed on Apr. 18, 2000, now Pat. No. 6,473,646.

(51) Int. Cl.[7] .............................................. A61N 1/365
(52) U.S. Cl. ........................................................ 607/19
(58) Field of Search .............................. 607/17–19, 27; 600/508, 510, 526, 587

(56) References Cited

U.S. PATENT DOCUMENTS

| 4,928,688 | A |   | 5/1990  | Mower ................. 128/419 PG |
|-----------|---|---|---------|-----------------------------------|
| 5,376,106 | A |   | 12/1994 | Stahmann et al. ............ 607/18 |
| 5,540,727 | A | * | 7/1996  | Tockman et al. ............. 607/18 |
| 5,792,203 | A |   | 8/1998  | Schroeppel ................... 607/30 |
| 5,891,176 | A | * | 4/1999  | Bornzin ....................... 607/18 |
| 6,021,351 | A | * | 2/2000  | Kadhiresan et al. .......... 607/19 |
| 6,044,298 | A |   | 3/2000  | Salo et al. .................... 607/17 |
| 6,273,856 | B1 |  | 8/2001  | Sun et al.                         |
| 6,473,646 | B2 | * | 10/2002 | Sun et al. ..................... 607/27 |

* cited by examiner

*Primary Examiner*—Kennedy Schaetzle
(74) *Attorney, Agent, or Firm*—Schwegman, Lundberg, Woessner & Kluth, P.A.

(57) ABSTRACT

A method for assessing cardiac function suitable for incorporation into an implantable cardiac rhythm management device. By measuring daily exertion levels in accordance with the invention, an assessment of cardiac function can be made that has been found to correlate well with conventional clinical classifications. The invention also provides for assessing cardiac function in conjunction with different pacing schemes designed to treat heart failure and using the assessment to select the best such scheme for the patient.

26 Claims, 2 Drawing Sheets

METHOD FOR ASSESSING CARDIAC FUNCTIONAL STATUS

CROSS-REFERENCE TO RELATED APPLICATION(S)

This patent application is a division of U.S. patent application Ser. No. 09/551,310, filed on Apr. 18, 2000, now issued as U.S. Pat. No. 6,473,646, the specification of which is incorporated herein by reference.

FIELD OF THE INVENTION

This invention pertains to systems and methods for delivering pacing and other therapies to treat cardiac conditions and for assessing the effectiveness of such therapies.

BACKGROUND

Congestive heart failure (CHF) is a clinical syndrome in which an abnormality of cardiac function causes cardiac output to fall below a level adequate to meet the metabolic demand of peripheral tissues. CHF can be due to a variety of etiologies with that due to ischemic heart disease being the most common. Symptoms of CHF in certain instances can be due to cardiac arrhythmias that are treatable with conventional bradycardia pacing. Some CHF patients suffer from some degree of AV block such that their cardiac output can be improved by synchronizing atrial and ventricular contractions with dual-chamber pacing (i.e., pacing both the atria and the ventricles) using a short programmed AV delay time. It has also been shown that some CHF patients suffer from intraventricular conduction defects (a.k.a. bundle branch blocks) such that their cardiac outputs can be increased by improving the synchronization of right and left ventricular contractions. Cardiac pacemakers have therefore been developed which provide pacing to both ventricles, termed biventricular pacing.

In CHF patients who are treated with pacing therapy (e.g., either a conventional pacemaker or a biventricular pacemaker), it is desirable to select a pacing scheme that optimally improves the patient's condition. Examples of a pacing scheme include a particular pacing mode and parameter values related to that mode such as lower rate limit, AV delay time, and biventricular delay time. Pacing schemes are conventionally selected based upon a clinical assessment of the patient's condition. For example, EKG data may indicate a patient is likely to be benefited more with biventricular pacing than with conventional dual-chamber pacing. After being set initially, the pacing scheme can then be adjusted on a trial and error basis to a more optimum one based upon the patient's history and physical examination in subsequent office visits. This also allows the pacing scheme to be adjusted in accordance with any changes that occur in the patient's physical condition. This method of assessing a CHF patient's cardiac functional status can be a very subjective one, however, depending on the physician's perception of the patient's symptoms and physical disability. There is a need, therefore, for a method of assessing a CHF patient's functional status that is more accurate and reproducible than those currently practiced in order to select a pacing scheme. It is toward this objective that the present invention is primarily directed.

SUMMARY OF THE INVENTION

The present invention relates to a method for assessing the functional status of congestive heart failure patients that is particularly suitable for use in selecting optimal pacing schemes for those patients receiving pacing therapy. In accordance with the invention, maximal exertion levels of the patient are tracked with an implantable device while the patient goes about his or her daily activities. Such maximal exertion levels have been found to correlate well with other methods of classifying a patient's cardiac functional status. In one embodiment, the method is performed by measuring a moving average over a specified averaging period of exertion levels attained by the patient during daily activities. Daily maximal exertion levels are then extracted from the measured moving average exertion levels for a specified number of days, and the patient's cardiac functional status is classified based upon the daily maximum daily exertion levels. The exertion levels are measured by a sensor that measures a physiological variable related to exertion level such as an accelerometer or minute ventilation sensor.

The method may be incorporated in a cardiac pacemaker used to treat congestive heart failure where the functional status assessment is used to either automatically select an optimum pacing scheme or to aid the clinician in making the selection. In such a device, a processor for controlling the operation of the device is programmed to perform the method using data collected from an exertion level sensor. The daily maximal exertion levels are registered and stored by the device, and may then be transmitted to an external programmer. The processor may also be programmed to automatically adjust a pacing scheme of the device based upon the extracted maximal exertion levels obtained during a testing sequence in which different pacing schemes are tried.

DESCRIPTION OF SPECIFIC EMBODIMENTS

Figure 1:
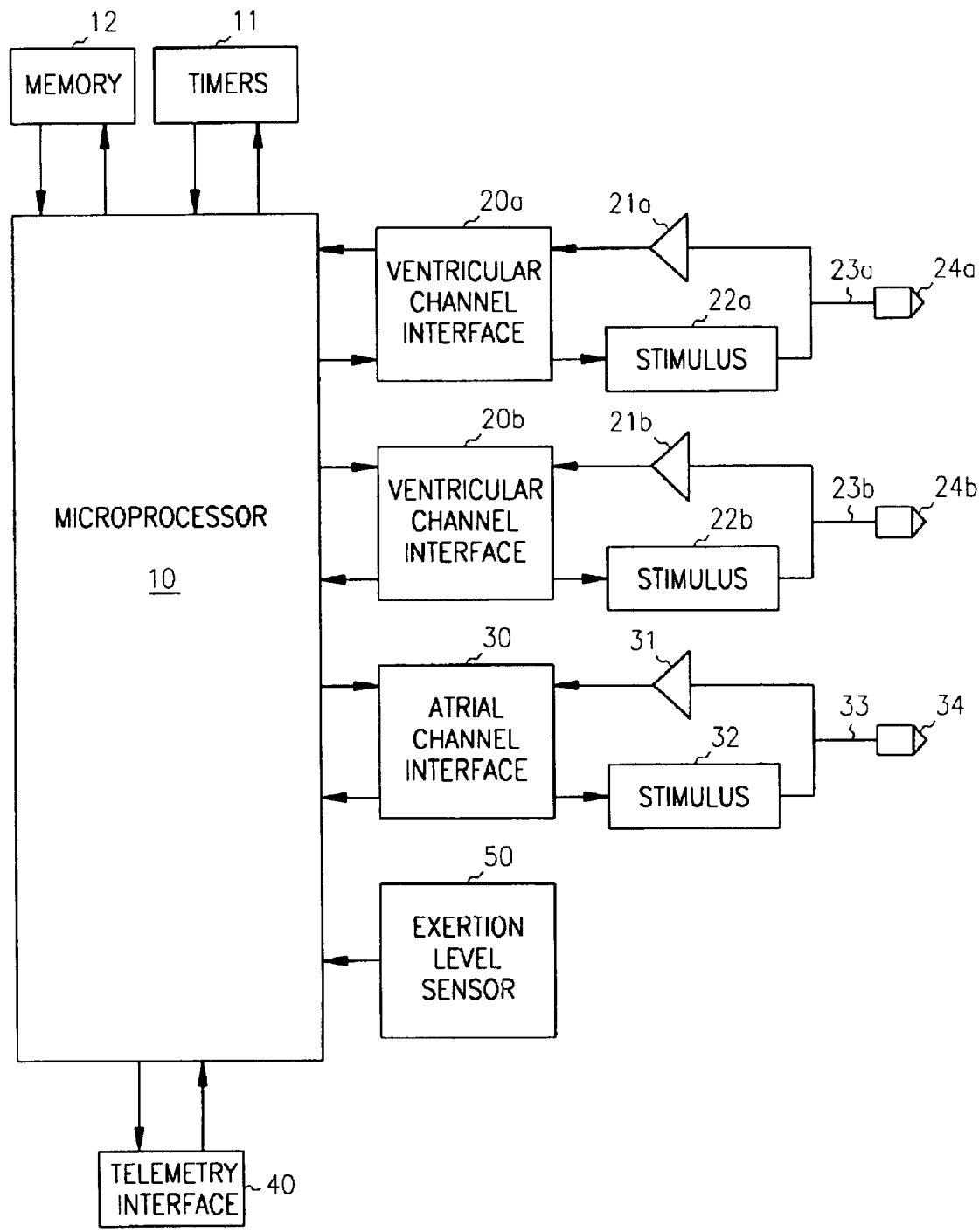
FIG. 1 is a system diagram of a pacemaker.

Assessing the functional status of a heart failure patient is usually done with a comprehensive history and physical examination. The physician's perception of the patient's symptoms and physical disability is then used to classify the patient's status according to a classification system such as that put forth by the Criteria Committee of the New York Heart Association (NYHA). It has been found that measured maximum exertion levels of a patient during daily living are well correlated to such classifications. In accordance with the invention, a patient's cardiac functional status is classified based upon measurements of maximal exertion levels attained by the patient as the patient goes about normal activities during the day. The exertion level measurements are performed by an implantable device such as a pacemaker or a portable external device. In a particular embodiment, exertion level signals from, e.g., an accelerometer and/or minute ventilation sensor are automatically collected by an implantable device and moving averaged over a period from 30 seconds to 10 minutes, with the daily maximum moving average value being registered and stored. The daily maximum moving average value is then averaged over a specified time period (e.g., on a weekly, monthly, or semiannual basis) with the resulting average maximum exertion level also registered and stored. By gathering exertion level data while different therapies are being tried, an indication of the effectiveness of the therapy in treating the patient's condition can be obtained.

The preferred way of implementing the exertion level measurements is to employ the same type of exertion level sensor used to control rate-adaptive pacemakers. A rate-adaptive pacemaker varies the pacing rate in accordance with a measured physiological variable related to metabolic rate or exertion level. (See, e.g., U.S. Pat. No. 5,376,106 issued to Stahmann et al., the disclosure of which is hereby incorporated by reference). Measuring minute ventilation, which is the product of ventilation rate and tidal volume, estimates oxygen consumption which is related to exertion level. Another way of determining exertion level is by measuring body activity or motion with either an accelerometer or vibration sensor. The activity-sensing pacemaker uses a microphone-like sensor (e.g., an accelerometer) inside the pacemaker case that responds to mechanical vibrations of the body by producing electrical signals proportional to the patient's level of physical activity.

The present invention can be used to assess the effectiveness of any therapy used to treat congestive heart failure or otherwise improve a patient's cardiac functional status. In the embodiments described below, the invention is incorporated into the control unit of an implantable pacemaker and used to evaluate different pacing schemes. Examples of such schemes include a particular bradycardia pacing mode, a lower rate limit, parameters related to rate-adaptive pacing, a programmed atrio-ventricular delay for dual-chamber pacing, and an interventricular delay for biventricular pacing. As noted above, biventricular pacemakers are sometimes used in the treatment of congestive heart failure where pacing pulses are delivered to both ventricles by separate electrodes during a cardiac cycle. (See, e.g., U.S. Pat. Nos. 5,792,203 and 4,928,688 which are hereby incorporated by reference). In a biventricular pacemaker, the right and left ventricles are sensed through separate channels with either both ventricles or only the left ventricle being paced upon expiration of a selected lower rate interval without receipt of a right ventricular sense signal, where the lower rate interval starts with either a pacing event or receipt of a right ventricular sense signal. In the case of biventricular pacing, the ventricles may be paced simultaneously or one after the other separated by a selected delay interval. The pacemaker may also be operated in a ventricular triggered mode where one or both ventricles are paced within a latency period following a sense signal from the right ventricle. Such different pacing schemes may vary in their effectiveness for any given patient, and the present invention provides a way of ascertaining which scheme is best.

Shown in FIG. 1 is a microprocessor-based pacemaker with the capability of delivering conventional bradycardia pacing to the atria and/or ventricles or biventricular pacing. (As used herein, the term pacemaker should be taken to mean any cardiac rhythm management device with a pacing functionality including an implantable cardioverter/defibrillator that includes a pacemaker). A microprocessor 10 is the primary component of the device's control unit and communicates with a memory 12 via a bidirectional data bus 13. The memory 12 typically comprises a ROM (read-only memory) for program storage and a RAM (random-access memory) for data storage. The pacemaker has atrial sensing and pacing channels comprising electrode 34, lead 33, sensing amplifier 31, pulse generator 32, and an atrial channel interface 30 which communicates bidirectionally with a port of microprocessor 10. The device also has ventricular sensing and pacing channels for both ventricles comprising electrodes 24a–b, leads 23a–b, sensing amplifiers 21a–b, pulse generators 22a–b, and ventricular channel interfaces 20a–b where "a" designates one ventricular channel and "b" designates the other. For each channel, the same lead and electrode are used for both sensing and pacing. The channel interfaces 20a–b and 30 include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. A telemetry interface 40 is also provided for communicating with an external programmer. An exertion level sensor 50 is provided to measure the patient's exertion levels in accordance with the invention as well as provide the capability for rate-adaptive pacing. The exertion level sensor may be a sensor for measuring a physiological variable related to the patient's level of physical exertion such as an accelerometer or a minute ventilation sensor.

Also shown interfaced to the microprocessor 10 are a number of interval timers 11 to be discussed below. These timers may either be discrete counters as shown or be implemented in software by the microprocessor executing programmed instructions in memory 12. A pacemaker is a device which paces one or more chambers based upon sensed events and the outputs of interval timers. In an atrial triggered pacemaker, timers for the following intervals are provided: lower rate interval (LRI) which defines the minimum rate at which the ventricles will be paced in the absence of spontaneous activity, atrioventricular delay interval (AVD) which defines the time delay between an atrial pulse or sense and the ensuing ventricular pace if no ventricular sense occurs in the interval, and atrial escape interval (AEI) which defines a minimum rate for atrial pacing in the case of an atrial paced mode. For biventricular pacing, an interval timer for the interventricular delay (IVD) is provided that defines the delay between the time the two ventricles are paced. The IVD, for example, can be set to zero to enable simultaneous pacing of the ventricles or can be set to a positive or negative value to enable sequential pacing of the two ventricles in the specified order and after the specified delay interval. Other interval timers are used to define refractory periods for the sensing channels during which time the channels are closed so that inputs are ignored.

In a particular embodiment of the invention, the method for assessing a patient's cardiac function as described above is implemented in the control unit of a pacemaker as illustrated in FIG. 1. In this embodiment, the effectiveness of different pacing schemes is tested by assessing the patient's cardiac function as different pacing schemes are tried. The test data is then employed to either automatically adjust the pacing scheme or is stored for later retrieval by a clinician. For example, a pacemaker with biventricular pacing capability might test four different pacing schemes on a CHF patient: left ventricular pacing with an AVD equal to 100 ms, left ventricular pacing with an AVD of 50 ms, biventricular pacing with an IVD of 0 and an AVD of 120 ms, and biventricular pacing with an IVD of 20 ms and an AVD of 180 ms. Each of these pacing schemes could be tried for a specified period (e.g., 30 days) with their effectiveness assessed by their effect on the patient's cardiac functional status as determined by the maximal exertion level method. In another example, a rate-adaptive bradycardia pacemaker having both an accelerometer and a minute ventilation sensor for measuring exertion levels might test three rate-adaptive pacing schemes: using the minute ventilation sensor only, using the accelerometer only, and using both sensors. A rate-adaptive pacemaker could also test different slope factors.

Figure 2:
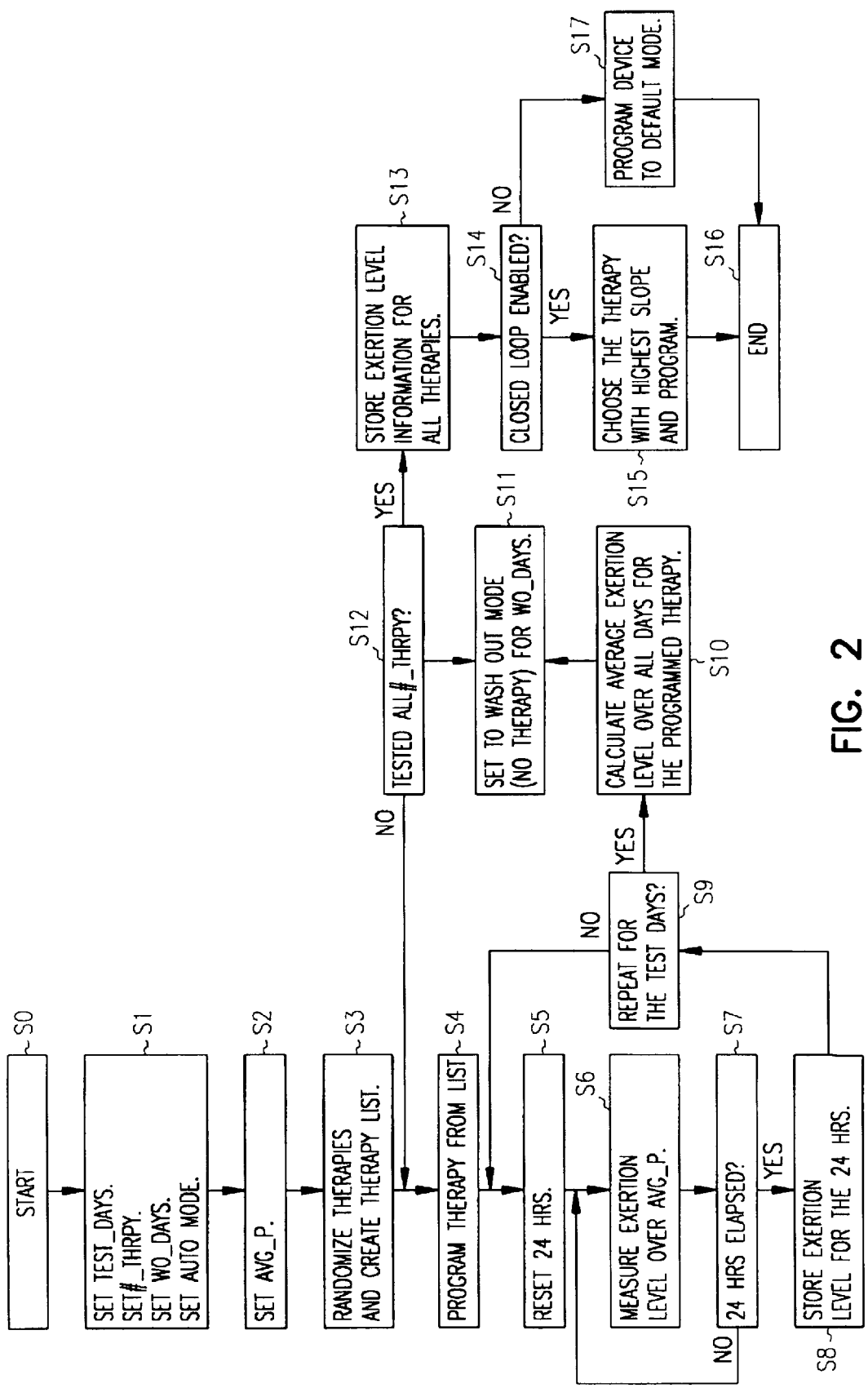
FIG. 2 is a flow chart illustrating the steps of an exemplary testing sequence.

FIG. 2 shows a flowchart of an exemplary version of the testing steps according to the present invention. The method starts (step S0) by performing any necessary initialization of variables. Various parameters used by the method are then set in accordance with preprogrammed values that may be modified by an external programmer (step S1): the number of wash out days (WO_DAYS) during which no therapy is delivered while cardiac function is assessed, the number of test days (TEST_DAYS) for which maximal exertion levels are to be determined, the number of therapies (e.g., pacing schemes) that are to be tested (#_THRPY), whether the pacing scheme is to be adjusted automatically in a closed-loop manner or not (AUTO), and the default pacing scheme (DFPS) that the device defaults to initially and reverts to if the AUTO switch is not in automatic mode. The averaging period AVG_P is then set (step S2), which is the period over which exertion levels are moving averaged before extraction of a maximal level as described above. The order of the therapies that are to be tested is then randomized, and a therapy list is created (step S3). The next therapy in the list is then programmed into the device (step S4). In this example, a daily maximal exertion level is determined, and the daily levels are then averaged over the total number of test days. A 24 hour timer is reset (step S5), and maximal exertion levels are then extracted from moving average data taken during the day. The maximal exertion levels are measured over the averaging period (step S6), and the step iterates until 24 hours have elapsed (step S7). Daily maximal exertion levels determined for the specified number of test days (step S9) which could be, for example, a week or a month. If so, an average daily maximal exertion level over the total number of test days is computed (step S10). The device is then configured to deliver no pacing therapy for a specified number of wash out days before the therapy is switched to the next one on the therapy list (step S11). It is next determined if all therapies on the list have been tested (step S12), and the next therapy on the list is tested (step S4) if not. Otherwise, the exertion level data for all of the therapies are stored (step S13). Depending on whether the automatic mode is enabled or not (step S14), either the therapy resulting in the best functional status for patient is selected for use by the device (step S15) or the device reverts to the default therapy (step S17), and the method is ended (step S16). Whether or not the automatic mode is enabled, the stored exertion level data is available for downloading to an external programmer and analysis by a clinician.

If the automatic mode is not enabled, the exertion level information associated with different therapies is displayed to the clinician upon interrogation of the device and can be used to select the best therapy. The stored exertion level data also provides a long-term history of maximal exertion levels that are representative of a patient's capability to perform physical activities and general state of health. Such a history may be useful to the clinician in making treatment decisions or in diagnosis.

Therapies other than pacing schemes may also be tested and evaluated by the method described above in which exertion levels are measured while different therapies are tried. This may involve selectively turning on or turning off different device therapeutic features to provide optimum therapy or reconfiguring parameter settings. For example, an implantable drug delivery device capable of delivering different drug therapies to treat conditions affecting a patient's cardiac functional status may use the present method to select the best therapy. A device can also be programmed to activate an additional diagnostic monitoring operation when there is a change in the patient's status as reflected by measured exertion levels. Such diagnostic monitoring may be normally turned for resource conservation or because the patient is required to exercise in order for the test to be performed. For example, rate dependent bundle branch block can be detected by activating AV delay monitoring when the exertion level is above a certain threshold.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A cardiac rhythm management device, comprising:

sensing channels for sensing atrial and ventricular depolarization signals, each channel including an electrode and a sense amplifier;

a pulse generator for delivering pacing pulses to the atrium and/or ventricle;

an exertion level sensor; and a processor for controlling the delivery of pacing pulses in response to elapsed time intervals and detected depolarization signals in accordance with a programmed mode, wherein the processor is programmed to perform a method comprising:

measuring a moving average over a specified averaging period of exertion levels attained by the patient during daily activities;

extracting daily maximal exertion levels from the measured moving average exertion levels for a specified number of days; and classifying the patient's cardiac functional status based upon the daily maximum daily exertion levels.

2. The device of claim 1 wherein the processor is programmed to automatically adjust a pacing scheme of the device based upon the extracted maximal exertion levels.

3. The device of claim 2 the processor is programmed to perform a testing sequence in which different pacing schemes are tried for predetermined periods and a patient's functional status is assessed while each scheme is tried.

4. The device of claim 3 wherein the processor is programmed to insert a wash out period between trials of different pacing schemes.

5. The device of claim 3 wherein the processor is programmed to automatically select for use the pacing scheme resulting in the most improved functional status of a patient as determined by the testing sequence.

6. The device of claim 1 wherein the processor is programmed to activate a diagnostic monitoring operation when there is a change in the patient's status as reflected by measured exertion levels.

7. A system for assessing a patent's cardiac functional status, comprising:

a sensor adapted to measure an exertion level; and a processor, coupled to the sensor, the processor adapted to:

calculate a moving averaged exertion level from the measured exertion level over a specified averaging period;

extract a maximal exertion level from the moving averaged exertion levels calculated over a first duration, the first duration including a plurality of the specified averaging periods; and classify the patient's cardiac functional status based on the maximal exertion durations extracted over a second duration, the second duration including a plurality of the first durations.

8. The system of claim 7, wherein the processor includes a first timer to time the specified averaging period, the specified averaging period ranging from 30 seconds to 10 minutes.

9. The system of claim 8, wherein the processor includes a second timer to time the first duration, the first duration being 24 hours.

10. The system of claim 7, wherein the first sensor is one of an accelerometer and a minute ventilation sensor.

11. The system of claim 10, further including a memory adapted to store at least the maximal exertion levels.

12. The system of claim 11, further including a display adapted to present at least the maximal exertion levels.

13. The system of claim 11, furthering including a drug delivery device adapted to deliver one or more drug therapies to the patient.

14. The system of claim 11, furthering including:
   at least one sensing channel adapted to sense a cardiac signal;
   at least one pacing channel adapted to deliver pacing pulses; and
   wherein the processor is adapted to control the delivery of the pacing pulses based on the cardiac signal and one of a plurality of pacing schemes, each of the plurality of pacing schemes including a particular pacing mode and a plurality of timing parameters.

15. The system of claim 14, wherein the processor is adapted to test the one of the plurality of pacing schemes and classify the patient's cardiac functional status in response to the one of the plurality of pacing schemes.

16. The system of claim 15, wherein the processor is adapted to adjust the one of the pacing schemes based on the classifications of the cardiac functional status associated with two or more of the plurality of the pacing schemes.

17. A cardiac rhythm management device, comprising:
   a first sensing channel adapted to sense a first cardiac signal;
   a first pacing channel adapted to deliver pacing pulses to a first cardiac site;
   a second sensing channel adapted to sense a second cardiac signal;
   a second pacing channel adapted to deliver pacing pulses to a second cardiac site;
   a first sensor adapted to measure a first exertion level;
   a processor, coupled to the first and second sensing channels, the first and second pacing channels, and the first sensor, the processor adapted to:
      calculate a moving average exertion level from the measured exertion level over a specified averaging period;
      extract a maximal exertion level from the moving average exertion levels calculated over a first duration, the first duration including a plurality of the specified averaging periods;
      classify the patient's cardiac functional status based on the maximal exertion durations extracted over a second duration, the second duration including a plurality of first durations; and
      control the delivery of the pacing pulses based on at least the first and second cardiac signals and a programmed pacing mode.

18. The device of claim 17, wherein the programmed pacing mode is a programmed rate-adaptive pacing mode, and wherein the processor is adapted to control the delivery of the pacing pulses based on at least the first and second cardiac signals, the first exertion level, and the programmed rate-adaptive pacing mode.

19. The device of claim 18, further including a second sensor adapted to measure a second exertion level, and wherein the processor is adapted to control the delivery of the pacing pulses based on at least the first and second cardiac signals, at least one of the first and second exertion levels, and the programmed rate-adaptive pacing mode.

20. The device of claim 19, wherein the first sensor includes an accelerometer and the second sensor includes a minute ventilation sensor.

21. The device of claim 19, wherein the first sensor includes a minute ventilation sensor and the second sensor includes an accelerometer.

22. The device of claim 17, further including:
   a third sensing channel adapted to sense a third cardiac signal;
   a third pacing channel adapted to deliver pacing pulses to a third cardiac site; and
   wherein the processor is adapted to control the delivery of the pacing pulses based on at least the first, second, and third cardiac signals, and the programmed pacing mode.

23. The device of claim 22, wherein the programmed pacing mode is a programmed rate-adaptive pacing mode, and wherein the processor is adapted to control the delivery of the pacing pulses based on at least the first, second, and third cardiac signals, the first exertion level, and the programmed rate-adaptive pacing mode.

24. The device of claim 23, further including a second sensor adapted to measure a second exertion level, and wherein the processor is adapted to control the delivery of the pacing pulses based on at least the first, second, and third cardiac signals, at least one of the first and second exertion levels, and the programmed rate-adaptive pacing mode.

25. The device of claim 24, wherein the first sensor includes an accelerometer and the second sensor includes a minute ventilation sensor.

26. The device of claim 24, wherein the first sensor includes a minute ventilation sensor and the second sensor includes an accelerometer.

* * * * *

UNITED STATES PATENT AND TRADEMARK OFFICE
CERTIFICATE OF CORRECTION

PATENT NO.   : 6,952,611 B2                                              Page 1 of 1
DATED        : October 4, 2005
INVENTOR(S)  : Sun et al.

It is certified that error appears in the above-identified patent and that said Letters Patent is hereby corrected as shown below:

Column 6,
Line 37, after "claim 2" insert -- wherein --.

Column 7,
Lines 14 and 17, delete "furthering" and insert -- further --.

Signed and Sealed this

Sixth Day of June, 2006

JON W. DUDAS
*Director of the United States Patent and Trademark Office*